United States Patent
Gladnick

(10) Patent No.: US 6,614,596 B2
(45) Date of Patent: Sep. 2, 2003

(54) SYSTEMS AND METHODS FOR INCREASING ILLUMINATION DENSITY WITHIN A FIELD OF VIEW OF AN IMAGING SYSTEM

(75) Inventor: Paul G. Gladnick, Seattle, WA (US)

(73) Assignee: Mitutoyo Corporation, Kawasaki (JP)

( * ) Notice: Subject to any disclaimer, the term of this patent is extended or adjusted under 35 U.S.C. 154(b) by 139 days.

(21) Appl. No.: 09/911,402

(22) Filed: Jul. 25, 2001

(65) Prior Publication Data

US 2003/0021112 A1 Jan. 30, 2003

(51) Int. Cl.[7] .............................................. G02B 27/14
(52) U.S. Cl. ....................... 359/630; 359/631; 359/633; 359/640
(58) Field of Search ................................ 362/231, 239, 362/240, 241, 33, 11, 328; 359/387, 389, 392, 629, 631, 633, 640, 630

(56) References Cited

U.S. PATENT DOCUMENTS

| | | | |
|---|---|---|---|
| 4,372,678 A | * | 2/1983 | Ikin et al. ...................... 355/37 |
| 4,567,551 A | * | 1/1986 | Choate ........................ 362/398 |
| 4,706,168 A | | 11/1987 | Weisner |
| 4,911,532 A | | 3/1990 | Hidaka |
| 5,461,417 A | * | 10/1995 | White et al. ................. 348/131 |
| 5,580,163 A | | 12/1996 | Johnson, II |
| 5,690,417 A | * | 11/1997 | Polidor et al. .............. 362/244 |
| 5,754,214 A | * | 5/1998 | Okino ........................ 347/229 |
| 5,880,889 A | | 3/1999 | Neumann et al. |
| 5,897,195 A | | 4/1999 | Choate |
| 6,179,439 B1 | * | 1/2001 | Choate ........................ 362/247 |
| 6,310,713 B2 | * | 10/2001 | Doany et al. ............... 359/247 |

* cited by examiner

Primary Examiner—Mohammad Sikder
(74) Attorney, Agent, or Firm—Oliff & Berridge, PLC

(57) ABSTRACT

An illumination system including a light emitting device which emits a beam of light, a lens for deflecting at least one axis of the beam of light and a reflective surface which aligns the light beam along an angle of incidence. The invention further includes a plurality of light emitting devices for creating a higher density beam of light with a prism for aligning the beams of light along an axis toward the lens, wherein the plurality of light emitting devices include a green light emitting device, red light emitting device and blue light emitting device.

38 Claims, 10 Drawing Sheets

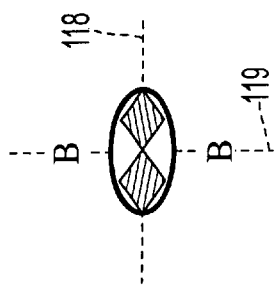
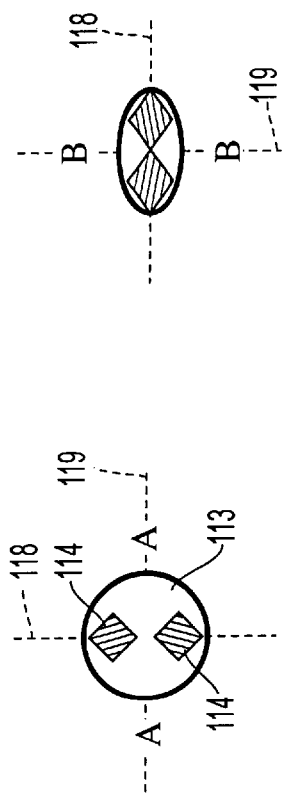
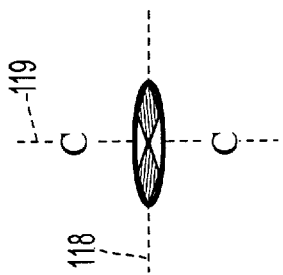
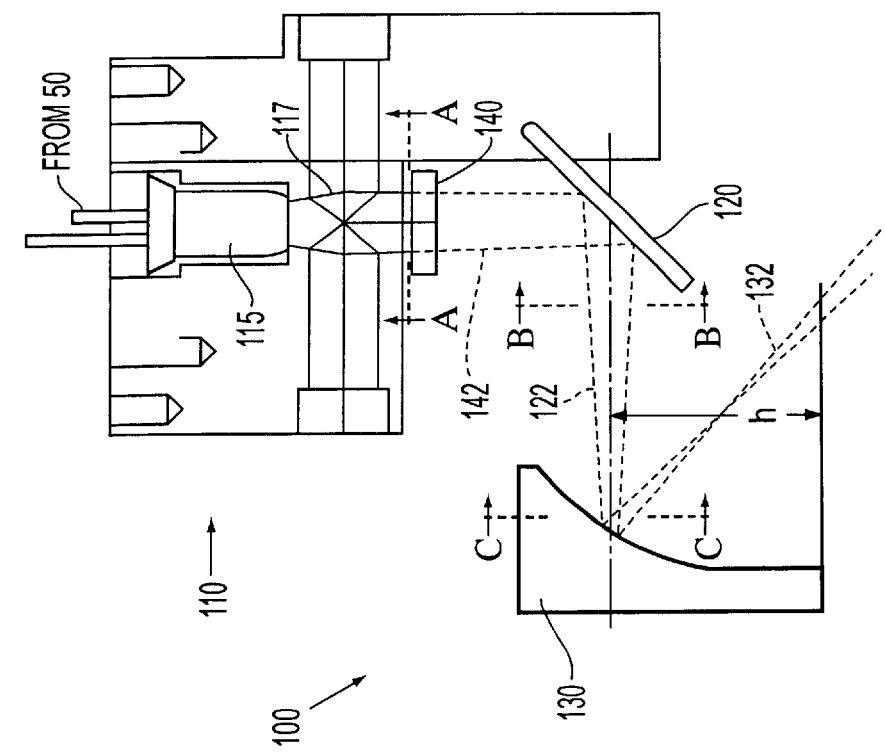

US 6,614,596 B2

SYSTEMS AND METHODS FOR INCREASING ILLUMINATION DENSITY WITHIN A FIELD OF VIEW OF AN IMAGING SYSTEM

BACKGROUND OF THE INVENTION

1. Field of Invention

This invention is directed to increasing the illumination density color within a field of view of an imaging system.

2. Description of Related Art

Uniform, diffuse illumination of a workpiece is often necessary in commercial vision systems to accentuate an edge of the workpiece within a designated field of view. Since most workpieces are not transparent, diffuse illumination of the workpiece is also necessary so that light which is reflected from the workpiece can be collected by an imaging system. Furthermore, an adjustable diffuse illumination source accommodates the observation and inspection of workpieces having a wide variety of shapes.

The adjustable illumination provides the ability to illuminate workpieces having different characteristics, such as, for example, shape, composition, and surface finish. In some systems, the intensity of light emitted by a light source is adjustable when the magnification of the imaging system is adjustable.

Also, conventional lighting systems project light onto the workpiece at an adjustable angle relative to an axis which is normal to the imaging plane. This angle is referred to as the angle of incidence. In many conventional vision systems, the axis normal to the imaging plane is parallel to, or coincides with, the optical axis of the vision system. Light projected at an angle of incidence which is between 0° and 90° may improve the surface contrast of the image and may also more clearly illuminate textured surfaces. Typically, such light sources have a prescribed range for the angle of incidence varying between 10° and 70°. Such a range is relatively broad and, therefore, provides adequate contrast in a variety of workpiece images.

Furthermore, conventional vision systems can also adjust or select the circumferential position of the source of diffuse lighting about an optical axis. Typically, the position of the diffuse lighting source is adjustable or selectable in, for example, addressable sectors or quadrants. As such, the field of view of the camera can be illuminated by any combination of sectors and quadrants of such a circular lighting system. Additionally, the intensity level of the light source can be coordinated with the circumferential position of the light source to optimize the illumination of a workpiece edge.

For example, some conventional vision systems include an annular light system that emits rectangular or toroidal patterns. The light system is an annulus which is divided into four quadrants. Other conventional vision systems include a ring light having an annulus which is subdivided into eight or more sectors. Additionally, some conventional vision systems have hemispherically-shaped light systems to direct light from a multitude of positions relative to an optical axis. The center of the hemisphere serves as a focal point for the light sources. Furthermore, any combination of sectors or quadrants can simultaneously be illuminated with varying illumination levels.

In other conventional programmable ring lighting systems, a very large number of fiber optic cables are arranged such that first ends of the fiber optical cables receive light from a high-intensity light source, such as a halogen lamp. The second ends of the fiber optic cables are arranged in a ring around the optical axis. The fiber optic cables, or sets of the fiber optic cables, can be individually controlled to project the light from the light source onto the field of view of the camera using an annular mirror and a parabolic annular mirror.

Recently, manufacturers of conventional vision systems have started offering a solid-state replacement for the traditional halogen lamps that have been used in conventional diffuse light sources. These manufacturers now offer light emitting diodes (LEDs) that offer high reliability, a longer service life, lower cost, good intensity modulation capabilities and a wide variety of frequency ranges.

One exemplary solid-state lighting system is disclosed in U.S. Pat. No. 5,580,163 to Johnson, II. As shown in FIG. 13, the 163 patent discloses a focusing light source with a flexible mount 502 for multiple light-emitting elements 504. Each light-emitting element 504 emits a beam of light onto a work piece 506 at a predetermined azimuthal angle $\alpha_n$ to form a predetermined pattern of light. To adjust or focus the multiple light-emitting elements 504, the flexible mount 502 is rotated in one direction toward the center of the mount 502 or a second direction away from the center of the mount 502. In various other embodiments, the light-emitting elements 504 can be separately colored light-emitting elements. To achieve multi-colored illumination, illumination from a plurality of the light-emitting elements 504 is combined at the workpiece.

The total azimuthal angle range corresponding to the sources used to achieve a particular multi-colored illumination is approximately $x\alpha_n$, where x is the number of different colored light-emitting elements 504 used. Thus, the multi-colored illumination provided by such a system cannot be controlled in azimuthal angle increments which are as narrow as the light emitting elements 504. Furthermore, any shadows in the field of view will exhibit zones of various colors, since each color component in the illumination is projected form a slightly different direction. Additionally, the illumination density, that is the illumination intensity projected onto the field of view on the workpiece from a given azimuthal angle range, is significantly limited by the characteristics of the individual conventional light-emitting elements 504.

Another exemplary lighting system is identified as prior art in the 163 patent itself. As a shown in FIG. 14 of the 163 patent, a beam of light is emitted from a light-emitting element 504 towards a work piece 506 at an angle of incidence β determined by the angle of the pivoting member 503. This exemplary lighting system generally suffers the previously discussed limitations of the lighting system of the 163 patent if solid-state sources are used for the light-emitting elements 504.

Furthermore, FIG. 14 illustrates another characteristic of conventional adjustable lighting systems. Conventional lighting systems emit a beam of approximately circular cross-section from each light-emitting element. The beams may also be collimated or focused. However, when a beam of light is emitted at an angle of incidence $\beta_1$ which is not normal to the illuminated workpiece surface, an approximately oval-shaped or elliptical pattern is created on a planar work piece 506 with an illumination field 512 having edges at a given $x_1$ and $y_1$ distance from the center of the illumination field 512, where $x_1$ is greater than $y_1$.

Moreover, as the angle of incidence increases as shown by $\beta_2$, when the beam intersects with a plane positioned along the optical axis 508 the distance $y_1$ of the illumination field 514 is approximately the same as $y_1$ of the illumination field 512, while the distance $x_2$ of the illumination field 514 becomes longer than $x_1$. Since the field of view along an optical system axis 508 is generally a circle centered about the optical axis, such elliptical illumination fields are not desirable for achieving the maximum illumination density for a given type of light-emitting element. For example, if the distance $y_1$ is set approximately at the edge of a circular field of view, the distance $x_1$ will extend beyond the edge of the field of view and a significant amount of available illumination energy will be wasted outside of the field of view.

Another exemplary solid-state lighting system is disclosed in U.S. Pat. No. 5,897,195 to Choate. The 195 patent discloses an oblique LED illuminator device with a cylindrical or truncated-conical array of LEDs. The array of LEDs produces collimated light beams that are directed onto axially-spaced, inclined surfaces formed on the outer periphery of a hollow, similarly-shaped Fresnel-like diffuser. The associated Fresnel-like diffuser refracts and directs rings of light beams onto the surface of a workpiece at variable angles of incidence. The array of LEDs coaxially surrounds the associated Fresnel-like diffuser. The associated Fresnel-like diffuser has annular, prism-shaped projections which differ in shape depending upon the desired angle of incidence. To create a beam of light with a desired angle of incidence, a light beam is emitted from an LED to the projection within the associated Fresnel-like diffuser, which redirects the light beam onto the workpiece at the desired angle of incidence. The lighting system of the 195 patent generally suffers the previously discussed limitations of the lighting system of the 163 patent when solid-state sources are used for the light-emitting elements.

Yet another exemplary solid-state lighting system is disclosed in U.S. Pat. No. 4,706,168 to Weisner, which is incorporated herein in its entirety. In the 168 patent, light from a ring source is directed toward a curved parabolic surface on a light collector ring. The curved parabolic surface substantially collimates the light and fans the light out radially toward a toroidal reflector surface on an encompassing ring. The relative angle of the light from the light source toward the parabolic surface and the position of the parabolic surface relative to the toroidal reflector surface determines the angle of incidence of a cone of light that falls in the region of the object, to illuminate particular features.

One exemplary method for combining light from a plurality of light sources is disclosed in U.S. Pat. No. 4,911,532 to Hidaka, which is incorporated herein by reference in its entirety. The 532 patent discloses a laser optical system with a single collimating lens and combining device. A collimating lens unit and a plurality of semiconductor lasers that emit laser beams of mutually different wavelengths are attached to the base of a light source unit. The laser beams are superposed one on top of another through dichroic prisms before impinging on the collimating lens. To superimpose the laser beams on top of each other, the optical axes and the diameters of the beams are adjusted by separate fine adjustment units.

An exemplary single dichroic prism is disclosed in U.S. Pat. No. 5,880,889 to Neumann et al., which is incorporated herein in its entirety. The 889 patent discloses a three-color dichroic beamsplitter/combiner usable to separate or combine unpolarized light. The beamsplitter/combiner separates a beam of light into three frequency bands corresponding to a first color, a second color, and a third color. The configuration of the glass support structure is chosen so that the first color of light is directed in a first direction, the second color of light is directed in a second direction, and the third color of light is directed in a third direction.

SUMMARY OF THE INVENTION

However, none of the 163, 195 and 168 patents disclose a lighting system for projecting a variable color along a single beam path when using a plurality of light sources. Furthermore, it should be appreciated that the optical energy available from relatively economical and compact solid state light emitting devices is relatively limited compared to conventional halogen light sources and fiber optic cable light sources. It should also be appreciated that none of the 163, 195 and 168 patents disclose techniques for combining a plurality of solid-state device light beams into a compound light-emitting element which provides a relatively high white-light illumination density along a relatively narrow azimuthal angle range in a lighting system. Furthermore, superimposing a plurality of laser beams with separate adjustment units can be especially difficult when the space for mounting the laser sources and their adjustment units is severely constrained. Superimposing the plurality of laser beams can also be difficult when using two dichroic prisms, as disclosed in the 532 patent.

This invention provides control systems and methods that enhance the diffuse lighting effects that are currently offered on the market.

This invention separately provides systems and methods that create conventional as well as more refined and versatile diffuse illumination using a simpler, more robust device.

This invention separately provides systems and methods that align a plurality of light beams from a set of two or more solid-state sources in a compact space.

This invention separately provides systems and methods that combine a plurality of light beams within a compound source.

This invention separately provides systems and methods that increase the illumination density available from a specific direction in an illumination field when using a combination of solid-state light sources.

This invention separately provides systems and methods that orient one or more solid-state light sources so that a beam of uneven optical energy distribution is oriented to provide a desirable illumination distribution in an illumination field.

This invention separately provides systems and methods that align the major axis of the cross-section of a shaped light beam relative to an optical path to provide a desirable illumination distribution in an illumination field.

This invention separately provides systems and methods such that the major axis of an illuminating light beam lies in a plane that is approximately normal to an optical axis of a system that receives images of objects illuminated by the light beam.

This invention separately provides systems and methods that align a plurality of light beams from a set of two or more of solid-state devices along a single beam path.

This invention separately provides systems and methods that create illumination containing a desired wavelength combination at a high level of spatial addressability.

In various exemplary embodiments, the control systems and methods of this invention include a light emitting source which emits a light beam containing at least one color of light, a lens that shapes the cross-section of the beam of light preferentially along at least one cross-section axis, and a reflective surface which reflects the beam of light along an angle of incidence. In other exemplary embodiments, the control systems and methods of this invention, further comprise a compound light emitting source comprising a plurality of light emitting devices with a prism that aligns the beams of light from the light-emitting devices along a single beam path toward the lens, where the plurality of light emitting devices include a green light emitting device, red light emitting device and blue light emitting device, thus creating a multiple wavelength light beam capable of supporting relatively high illumination densities.

Further, in other exemplary embodiments, the lens is a Fresnel lens which shapes the cross-section of the beam of light to create an elliptically-shaped cross-section with a major axis and a minor axis, where the major axis lies in a plane that is approximately normal to an optical axis of a system that receives images of objects illuminated by the light beam. Additionally, in other exemplary embodiments, the reflective surface comprises a first reflective surface and a second reflective surface. The beam of light is reflected perpendicularly by the first reflective surface onto a particular portion of the second reflective surface. The particular portion of the second reflective surface aligns the beam of light along the angle of incidence. The first reflective surface and second reflective surface are movable relative to each other to create the angle of incidence.

An exemplary embodiment of the systems and methods of this invention further incorporates the systems and methods for illuminating objects for vision systems as described in the 168 patent, and a three color dichroic beam combiner similar to the dichroic beamsplitter/combiner described in the 889 patent.

These and other objects of the invention will be described in or be apparent from the following description of the exemplary embodiments.

BRIEF DESCRIPTION OF THE DRAWINGS

The invention will be described in conjunction with the following drawings in which like reference numerals designate like elements and wherein:

FIGS. 2 is a side sectional view of a first exemplary embodiment of a portion of the illumination system of FIG. 1;

FIGS. 3–5 illustrate the shape of the cross-section of the light beam at various points along the beam path of the portion of the illumination system shown in FIG. 2.

DETAILED DESCRIPTION OF EXEMPLARY EMBODIMENTS

Figure 1:
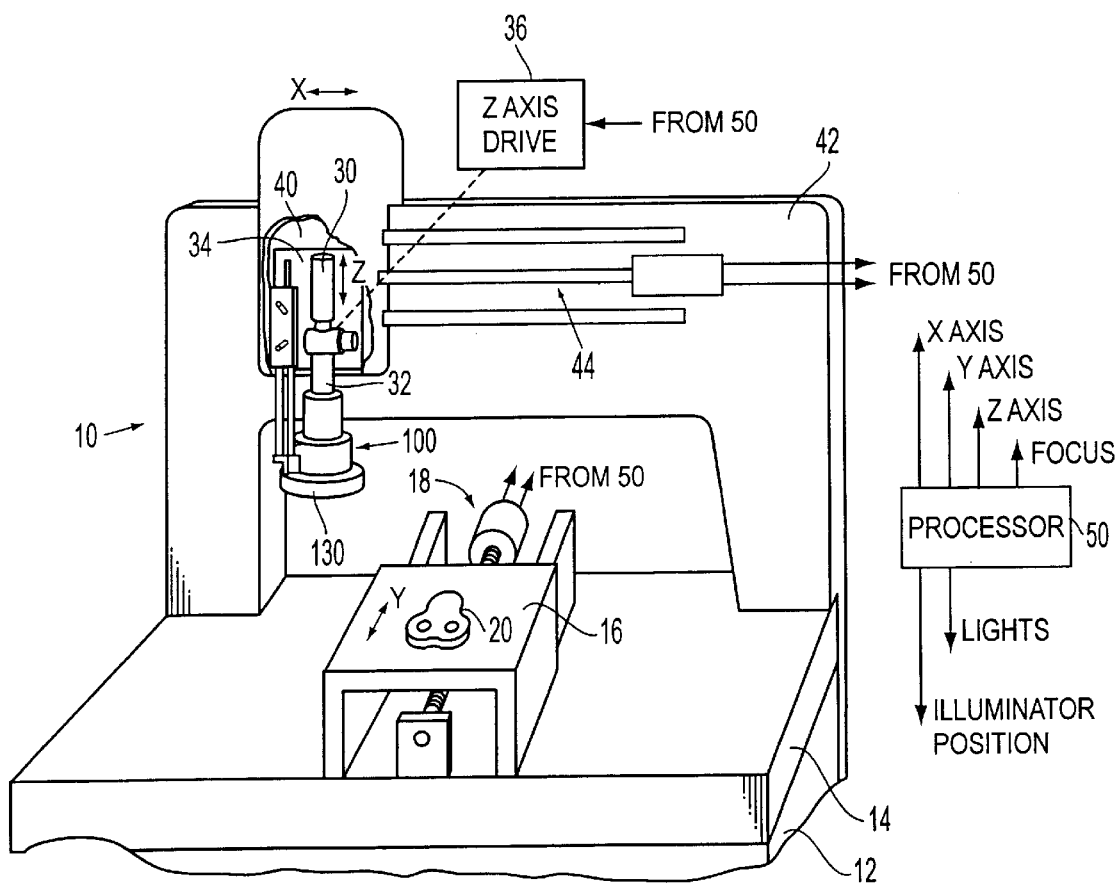
FIG. 1 is a perspective view, partially broken away, of a vision system incorporating an illumination system in accordance with the invention.

A vision system 10 in accordance with the invention, as shown in FIG. 1, comprises a base console 12 having a table 14. A stage 16 is movable in the Y direction along the stage 14 under the control of a drive 18. The drive 18 includes a motor and lead screw. A vertically mounted camera 30 views the workpiece 20 through an optical system 32. The stage 16 is movable to place a workpiece 20 to be inspected, indicated only generally, at a given position in a field of view of the camera 30.

The camera 30 is mounted on a Z-axis support 34 that is driven in the vertical direction by a Z-axis motor 36 so that the camera 30 can focus on particular regions and surfaces of the workpiece 20 that lie within the field of view. The camera 30 and the Z-axis support 34 are stably mounted on an X-axis carriage 40 that is mounted on a stable, vibration-free bridge 42 spanning the field of view above the stage 16. The carriage 40 is translated in the horizontal plane by a drive 44 comprising a motor and lead screw. The drives 18 and 44, as well as the Z-axis drive motor 36, are controlled by signals from a processor 50, which is typically programmed to position the workpiece 20 at given X and Y axis positions relative to the camera 30 and also to focus the camera 30 on a particular level of the workpiece 20. An illumination system 100 having elements concentric with the optical axis of the optical system 32 is mounted conjointly with the camera 30 and the optical system 32 on the Z-axis support 34.

In various exemplary embodiments, as shown in FIG. 2, the illumination system 100 includes a light source 110, a first reflective surface 120 and a second reflective surface 130. Each light source 110, includes at least one solid-state light emitting device 115 and a lens 140.

Each solid-state light emitting device 115 may be an LED, a laser diode or any other known or later-developed solid-state light emitting structure. Further, each solid-state light emitting device 115 may emit radiation in the ultra-violet, visible and/or near infrared regions of the electromagnetic spectrum. Each solid-state light emitting device 115 is selected because it emits radiation in the spectral regions in which the electronic imaging elements, such as a charge-coupled device, of the electronic or digital camera 30 are known to be photosensitive.

LEDs are also used as the solid-state light emitting devices 115 because LEDs are more amenable to precise optical power regulation than halogen lamps. This is at least partially due to the smaller drive currents needed to operate the LEDs. In addition, the discrete nature of LEDs allows the wavelength of the emitted light to be more flexibly selected. Also, when driven electronically within the working parameters of the LEDs, the repeatability and reliability of a light intensity output by the LEDs are both very high. In addition, some LEDs are capable of emitting light in the ultra-violet, a frequency range that improves the resolving power of imaging optics. Laser diodes may also be used for the solid-state light emitting devices 115.

Each of the light sources 110 may have one or more optical power monitoring devices incorporated within that light source 110. When used, the optical power monitoring device is, in various exemplary embodiments, a silicon photodiode whose spectral responsivity is matched to the spectral emission of the solid-state light emitting devices 115 within the light source 110. These optical power monitoring devices are not restricted by material or design. Any known or later-developed device capable of measuring the optical output of the solid-state light emitting devices 115 within the light source 110 can be used. In a configuration where each light source 110 can switch between different ones of a number of solid-state light emitting devices 115 that emit light of different illumination colors, the light source 110 can have a dedicated optical power monitoring device for each light emitting device 115. Some commercially available solid-state light emitting devices have a built-in detector that outputs a signal indicating the optical power being output from the device. Thus, the optical power monitoring device for each light emitting device 115 may be built into the device or a separate part of the light source assembly.

As shown in FIG. 2, a beam of light 117 is emitted from the light emitting device 115. As shown schematically in FIG. 3, the inventor has recognized that the cross-section of the beam of light 117 emitted from various exemplary solid-state light emitting devices 115 includes one or more emission areas 114 which provide most of the optical energy of the beam and one or more non-emission areas 113 which carry little or no optical energy. The non-emission areas 113 may be caused, for example, by wire bond contact areas on the light-emitting device 115.

The inventor has found that, in order to achieve the best illumination density and distribution in an illumination field on a workpiece, there is a desired orientation for the one or more emission areas 114 within the beam of light 117. In various exemplary embodiments according to this invention, the desired orientation for the one or more emission areas 114 is achieved by placing the light emitting device 115, in a desired orientation with due regard to the effects of optical elements in the illumination system optical path between the light emitting device 115 and the workpiece 20.

In various exemplary embodiments of the lighting system 100, the preferred orientation of the light emitting device 115 is determined by testing various orientations and observing the illumination density and distribution in an illumination field on a workpiece using suitable measuring instruments or by analyzing the image data provided by the vision system 10. For example, the orientation which yields the highest average illumination density or an adequate and controlled illumination density in the field of view, is determined and selected. Other criteria, such as the orientation that provides the most uniform illumination density in the field of view or the overall illumination field, may also be used. A full range of orientations may be tested by mounting the light emitting device at various orientations covering a 360 degree range of rotation relative to the light source 110.

FIGS. 3–5 show an exemplary orientation of the exemplary emission area 114 in the beam of light 117 for the configuration of optical elements in the illumination system optical path for the exemplary lighting system 100. The exemplary orientation of the exemplary emission area 114 also determines the preferred mechanical orientation of the exemplary light emitting device 115.

As further shown in FIG. 2, the beam of light 117 passes through the lens 140 to create a first modified beam of light 142. As shown in FIG. 3, the emitted beam of light 117 is in various exemplary embodiments approximately the same size as the lens 140. As should be appreciated, a higher density, but smaller cross-sectional area, emitted beam of light 142 would be produced if the beam of light 117 were smaller than the lens 140. Conversely, if the beam of light 117 were larger than the lens 140, the emitted beam of light 117 that could not fit within the lens 140 would be wasted. Thus, when the emitted beam of light 117 is approximately the same size as the lens 140, i.e., critically fills the lens 140, a lower intensity light emitting device 115 could be used without wasting energy created by the light emitting device 115.

In various exemplary embodiments, the lens 140 is a Fresnel lens or a cylindrical lens selected according to the desired characteristics to be obtained in the first modified beam of light 142. In various exemplary embodiments of the systems and methods according to this invention, and in particular for the configuration of optical elements in the illumination system optical path for the exemplary lighting system 100, the Fresnel lens or cylindrical lens 140 is of a form and orientation that shapes the cross-section of the emitted beam of light 117 into an approximately elliptical first modified beam of light 142. The cross-section of the beam of light 117 is essentially unchanged by the lens 140 with respect to a first axis 118, which is the major axis of the elliptical first modified beam of light 142. The beam of light 117 is focused by the lens 140 to converge along second axis 119 of the emitted beam of light 117, which is perpendicular to the first axis 118. This second axis 119 is the minor axis of the elliptical first modified beam of light 142. It should be appreciated, when the beam of light converges along the minor axis 119 of the elliptical first modified beam of light 142, the cross-section of the beam of light 142 constricts toward the major axis 118.

The elliptical first modified beam of light 142 is then reflected by the first reflective surface 120 to create a second modified beam of light 122. Because the reflective surface 120 is in the path of the light source 110, the reflective surface 120 deflects the light radially outwardly relative to the reflective surface 120 to form the second modified beam of light 122. Thus, the second modified beam of light 122 is for the most part projected perpendicular to the optical axis of the camera 30. Thus, the reflective surface 120 acts as a light path diverter which changes the direction of the modified beam of light. As shown in FIG. 4, the dimension of the cross-section of the second modified beam of light 122 along the minor axis 119 continues to constrict toward the major axis 118 as it is projected toward a second reflective surface 130 located radially outside of the first reflective surface 120.

Figure 6:
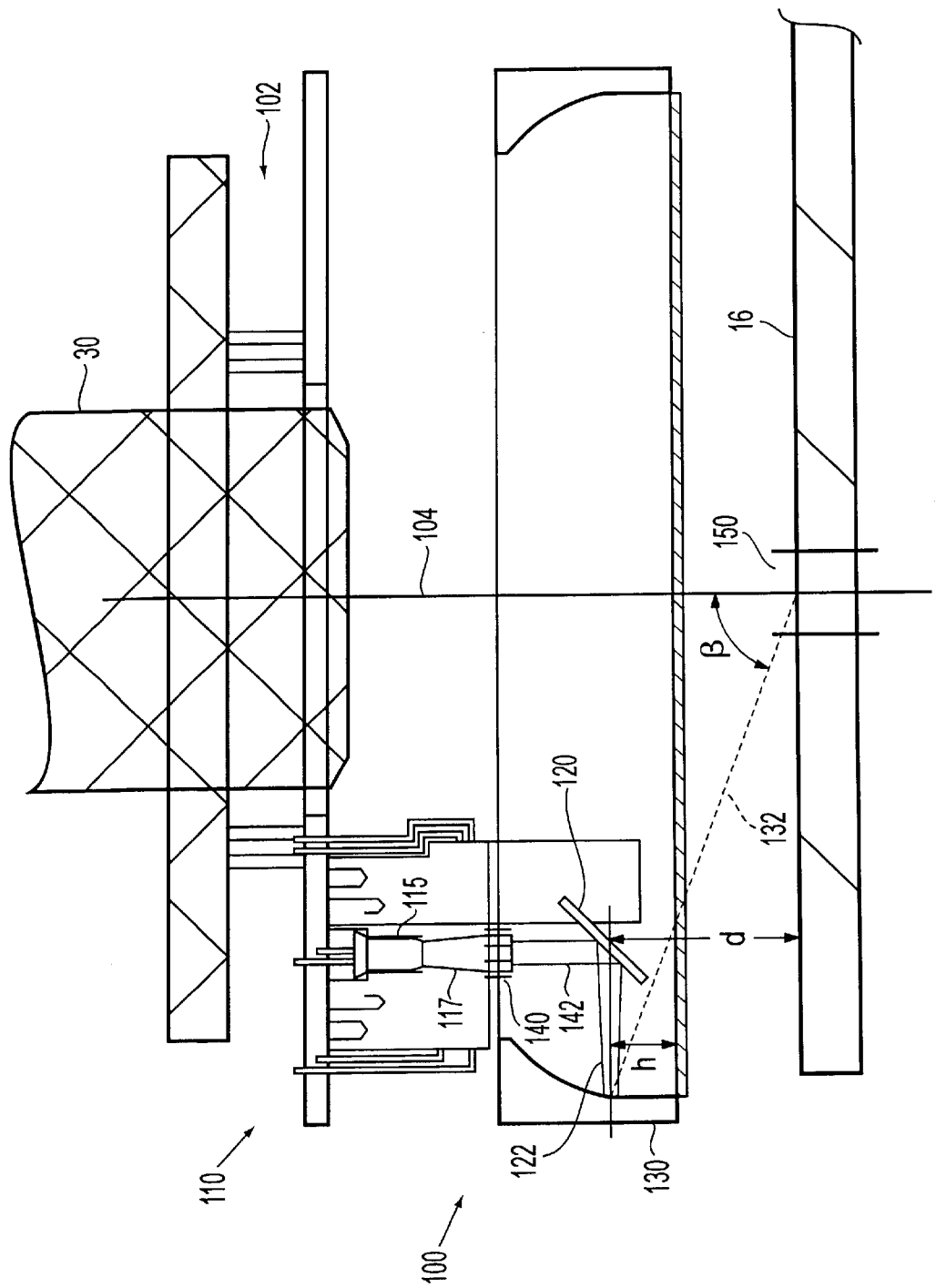
FIG. 6 is a side sectional view of a portion of the vision system of FIG. 1 incorporating the first exemplary embodiment of FIG. 2.

The outwardly-directed second modified beam of light 122 then reflects from the second reflective surface 130, to form a third modified beam of light 132, as shown in FIGS. 2 and 6. In various exemplary embodiments the first reflective surface 120 and the second reflective surface 130 are surface portions or facets on respective annuli oriented in a horizontal plane in FIGS. 2 and 6. The second reflective surface 130 is movable relative to the first reflective surface 120 along the Z-direction.

As shown in FIG. 5, as the second modified beam of light 122 strikes the second reflective surface 130, the dimension of the cross-section beam of light 122 along the minor axis 119 of the elliptically-shaped second modified beam of light 122 has substantially constricted to the major axis 118. At the same time, the dimension of the cross-section beam of light 122 along the major axis 118 is unchanged if the first reflective surface 120 is a flat facet. Alternatively, the dimension of the cross-section beam of light 122 along the major axis 118 is slightly larger if the first reflective surface 120 is a circular mirror. For the configuration of optical elements in the illumination system optical path for the exemplary lighting system 100 shown in FIG. 2, due to the convergence of the beam of light 122 along the minor axis 119 and the focusing effect of the second reflective surface 130, the beam of light 132 will converge approximately to a line extending along the major axis 118 proximate to the second reflective surface 130, and then will diverge along the minor axis 119 in order to fill an illumination field 150.

It should be appreciated that a primary consideration in the exemplary embodiment described above is that most or all of the optical energy in the beam 117 arrives within the desired illumination field 150, and that little or no optical energy is wasted outside of the optical path of the illumination system or outside of an expected field of view within the desired illumination field 150. Accordingly, in various exemplary embodiments, the converging and diverging characteristics of the beams of light 142, 122 and 132, along either the minor or major axes, may vary from the foregoing description while still providing that most or all of the optical energy in the beam 117 arrives within a desired illumination field 150, and that little or no optical energy is wasted outside of the optical path of the illumination system or outside of an expected field of view within the desired illumination field 150. In contrast with many commercially available illumination systems, which waste optical energy in an illumination field much larger than the field of view of an associated vision system, in various exemplary embodiments, the illumination system configuration of FIG. 2 provides an illumination field which does not create an illumination field that is significantly larger than the field of view. For example, in various exemplary embodiments, the illumination field 150 has no dimension that is greater than approximately twice the maximum dimension of the field of view of an exemplary vision system used in conjunction with the illumination system.

As shown in FIG. 6, in various exemplary embodiments, the reflective surface 130 has a parabolic cross section. A parabolic cross section is adequate for many illumination systems, although it should be appreciated that a hyperbolic curve may also be used. The position at which the second modified beam of light 122 from the first reflective surface 120 impinges on the curved reflective surface 130 determines the angle of incidence β of the third modified beam of light 132 on the stage 16.

Figure 7:
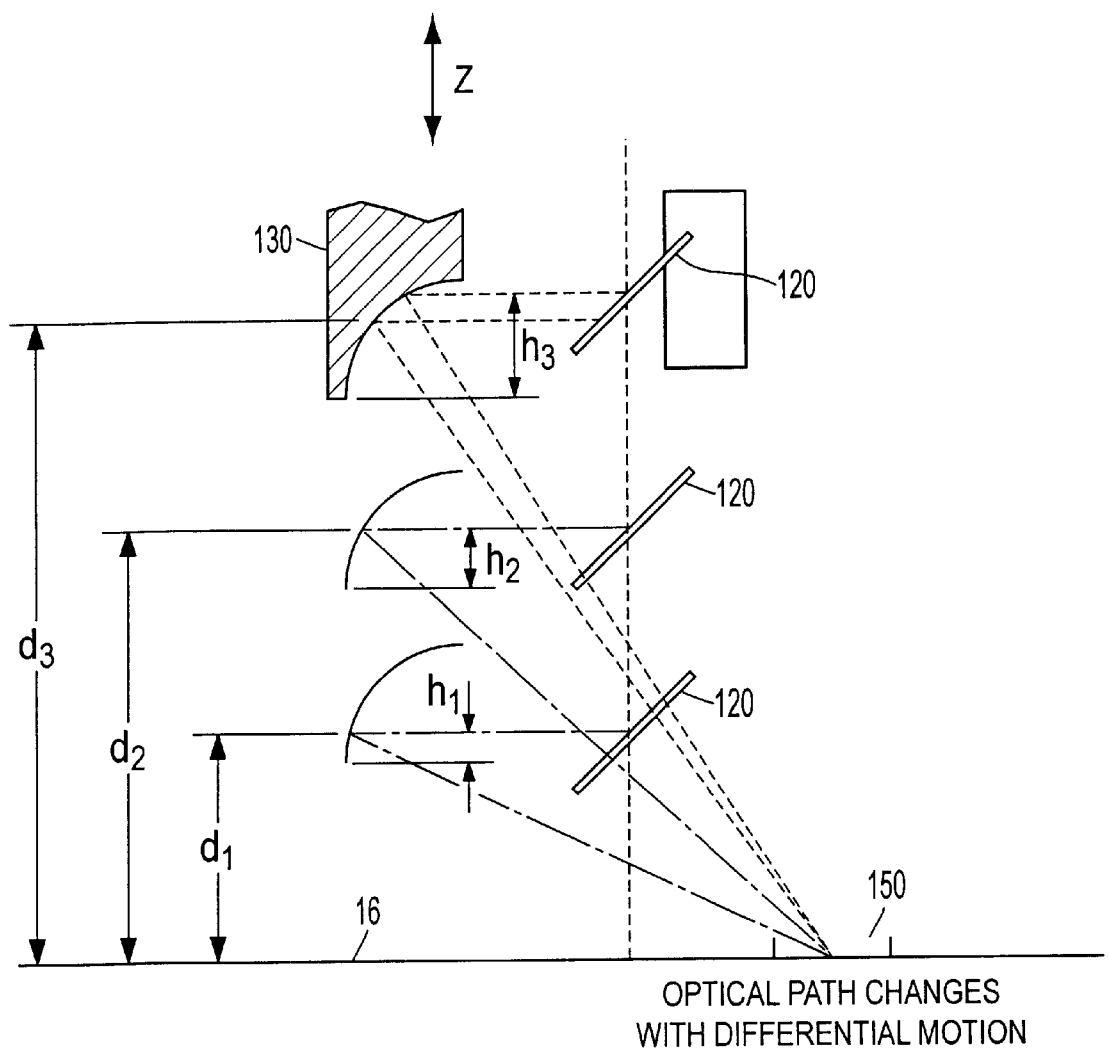
FIG. 7 is a simplified depiction of variations in the angle of incidence provided by different relative positions of the reflectors in the system of FIGS. 1–6.

As shown in FIG. 7, to change the angle of incidence, the two reflective surfaces 120 and 130 are moved together along the z-axis to the extent that is required for the illumination system to illuminate the illumination field 150, but are moved relative to each other along the z-axis to the extent required to achieve the desired angle of incidence. Thus, the beam of light 122 from the first reflective surface 120 impinges on a different region of the reflective surface 130 to change the angle of incidence and to maintain the desired illumination field location.

As shown in FIG. 7, the reflective surfaces 120 and 130 are movable relative to each other and to the stage 16 along the Z-axis. To maintain the third modified beam of light 132 at the same location coincident with the filed of view of the vision system on the stage 16 or the workpiece 20 as the angle of incidence B changes, it should be appreciated that, as the distance d between the reflecting surface 120 and the stage 16 increases, the distance h between the bottom of the reflecting surface 130 and the major axis 118 of the second modified beam of light 122 increases. Conversely, as the distance d between the reflecting surface 120 and the stage 16 decreases, the distance h between the bottom of the reflecting surface 130 and the beam of light 132 decreases.

Figure 8:
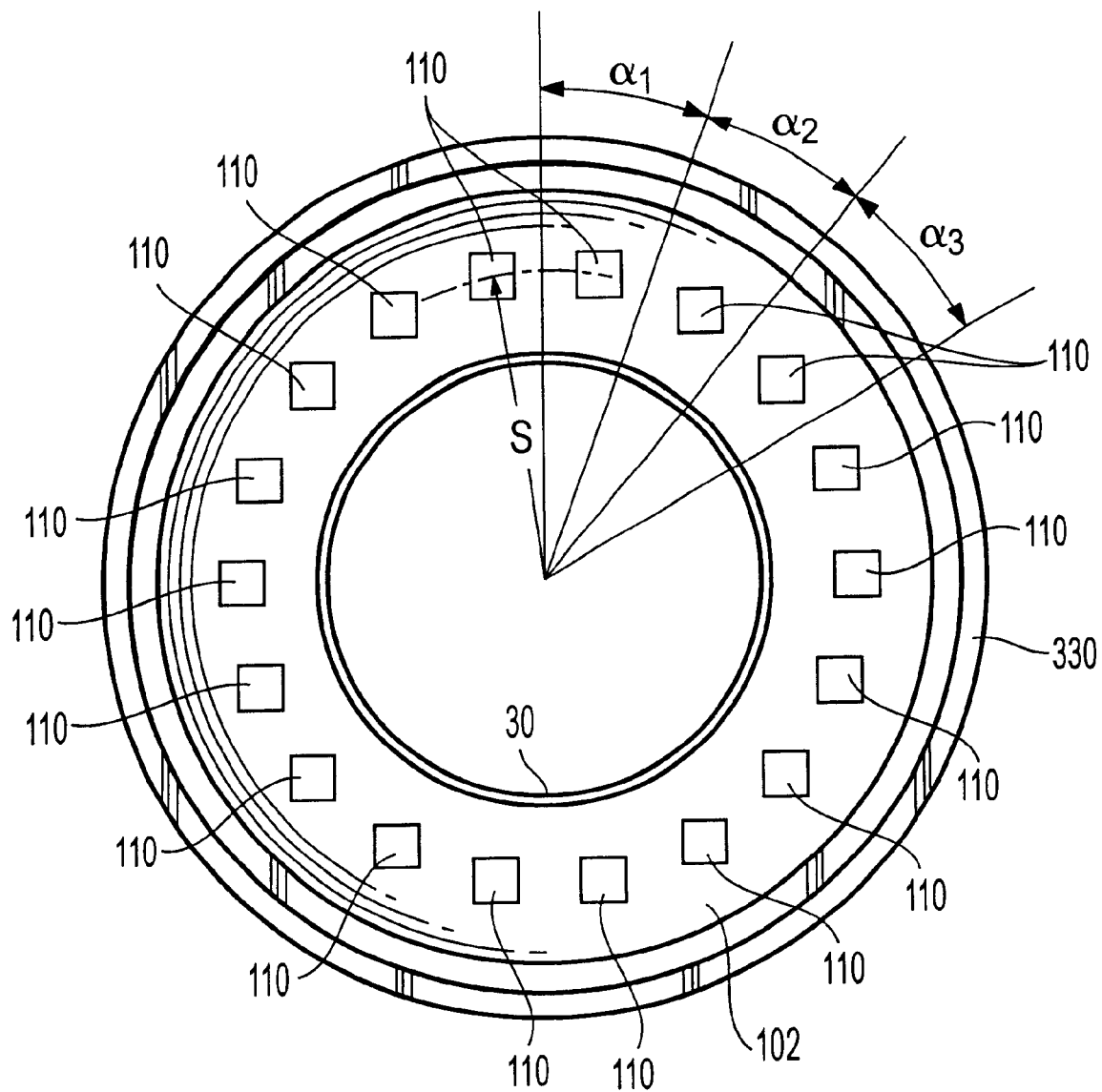
FIG. 8 is a simplified plan view showing the arrangement of light sources in the portion of the illumination system shown in FIG. 2.

As shown in FIGS. 6 and 8, a plurality of the light sources 110 are used to surround the workpiece 20 with a pattern of lighting. In various exemplary embodiments, a support system 102 of the illumination system 100 is placed around the camera 30 to support the plurality of light sources 110. The plurality of light sources 110 surrounds the optical axis 104 and is located outside of the optical path of the camera 30.

To create a pattern of lighting around the workpiece 20, each light source 110 is separated by a predetermined azimuthal angle increment α from a neighboring light source 110. When a beam of light 117 is emitted from a single one of the light sources 110, the resulting third modified beam of light 132 is directed along an azimuthal angle $α_n$. The azimuthal angle increment α is generally, but not necessarily, determined such that, given the physical dimensions of the light source 110, the maximum number of light sources 110 can be placed at a radial distance S from the optical axis 104. Furthermore, the number of light sources 110 used is also dependent on the desired light intensity created by any amount of overlap of, or amount of space between, the third modified beams of light 132.

In various exemplary embodiments, the major axis 118 of the cross-section of the second modified beam of light 122 is oriented in a "horizontal" plane i.e., a plane perpendicular to the optical axis 104. When the major axis 118 of the second modified beam of light 122 is oriented in a horizontal plane, that is the plane of the annular reflecting surface 130, the beam of light is more concentrated at a particular distance h from the bottom of the reflecting surface 130 and thus the curvature of the reflective surface 130 causes less distortion in the third modified beam of light 132 and more desirable illumination results. Furthermore, when the major axis of the cross-section of the third modified beam of light 132 is oriented in a horizontal plane, a desirable near-circular shape of the illumination field 150 is achieved for most illuminated surfaces, as described below with respect to FIG. 14.

Figure 14:
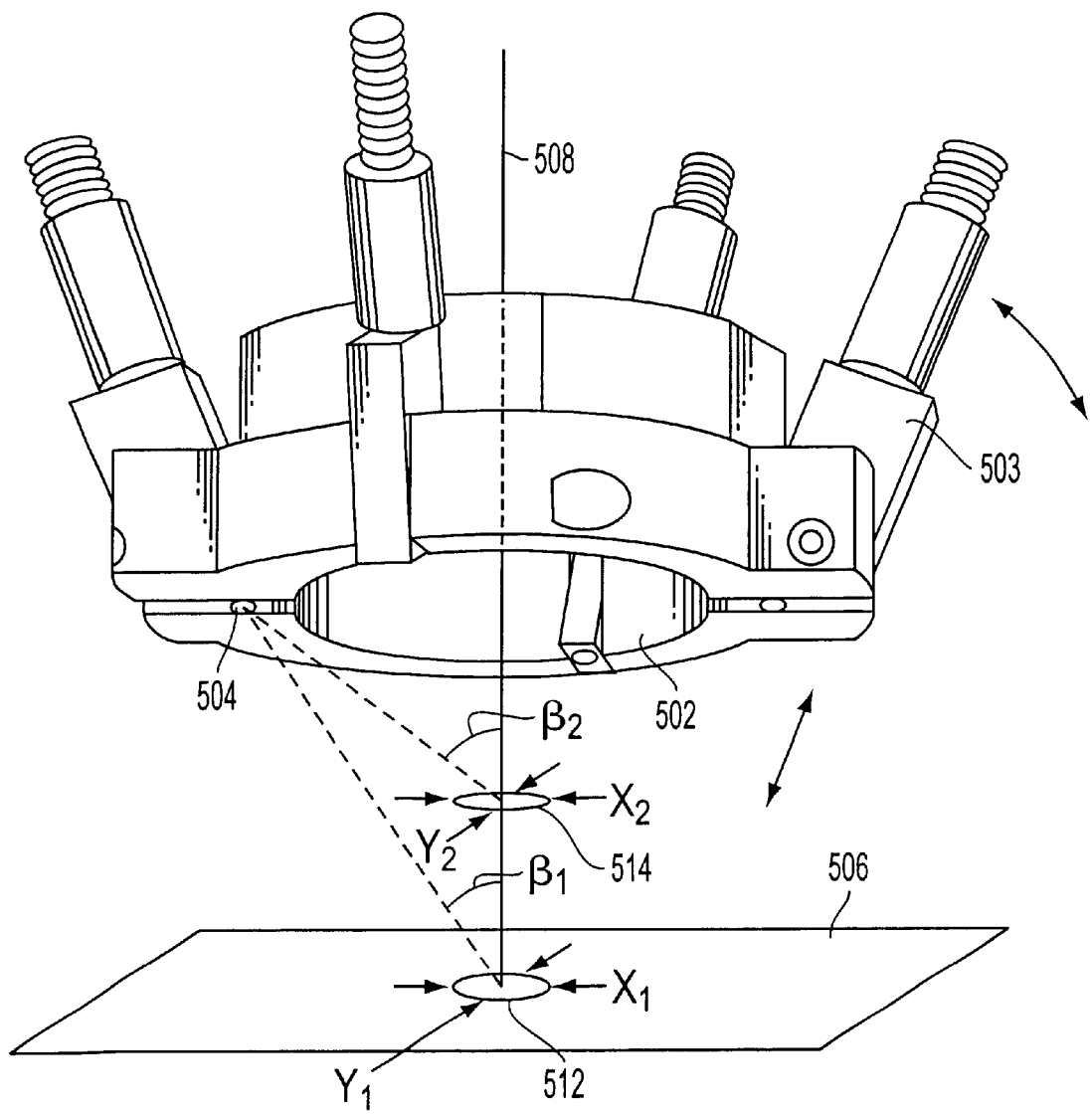
FIG. 14 is an example of typical illumination field patterns on a workpiece from a lighting system according to the related art.

As shown in FIG. 14, conventional lighting systems emits a beam of approximately circular cross-section from each light-emitting element. The beams may also be collimated or focused. However, when a beam of light is emitted at an angle of incidence $β_1$ which is not normal to the illuminated workpiece surface, an approximately oval-shaped or elliptical pattern for a first illumination field 512 is created on a planar work piece 506. The first illumination field 512 has edges at a given $x_1$ and $y_1$ distance from the center of the illumination field 512, where $x_1$ is greater than $y_1$. Furthermore, as the angle of incidence increases, as shown by $β_2$, when the beam intersects with a plane positioned along the optical axis 508, the distance $y_1$ of a second illumination field 514 is approximately the same as $y_1$ of the first illumination field 512. However, while the distance $x_2$ of the second illumination field 514 is longer than $x_1$.

Since the field of view along an optical system axis 508 is generally a circle centered about the optical axis, such elliptical illumination fields are not desirable when attempting to achieve the maximum illumination density for a given type of light-emitting element. For example, if the distance $y_1$ is set approximately at the edge of a circular field of view, the distance $x_1$ will extend beyond the edge of the field of view. As a result, a significant amount of available illumination energy will be wasted outside of the field of view. In contrast, in the illumination system according to this invention the major axis 118, of the cross-section of the third modified beam of light 132 is oriented in a horizontal plane according to the various exemplary embodiments of the systems and methods of this invention. As a result, the previously-described lengthening of the illumination field in the x-direction, due to the angle of incidence on a workpiece surface, effectively lengthens the minor axis 119 in the illumination field as the beam intersects an approximately horizontal illuminated surface. Consequently, a desirable near-circular shape of the illumination field 150 is achieved.

It should be appreciated that it is conventional for the extent of the field of illumination 150 to exceed the extent of the field of view of the vision system. However, even in such a case, shaping the light beam and the orientation of major and minor light beam axes 118 and 119 as described herein still provides a more uniform illumination density, and a relatively higher average illumination density in an illumination zone that fills or overfills the field of view of the vision system, compared to light beams provided by the conventional illumination systems.

Figure 9:
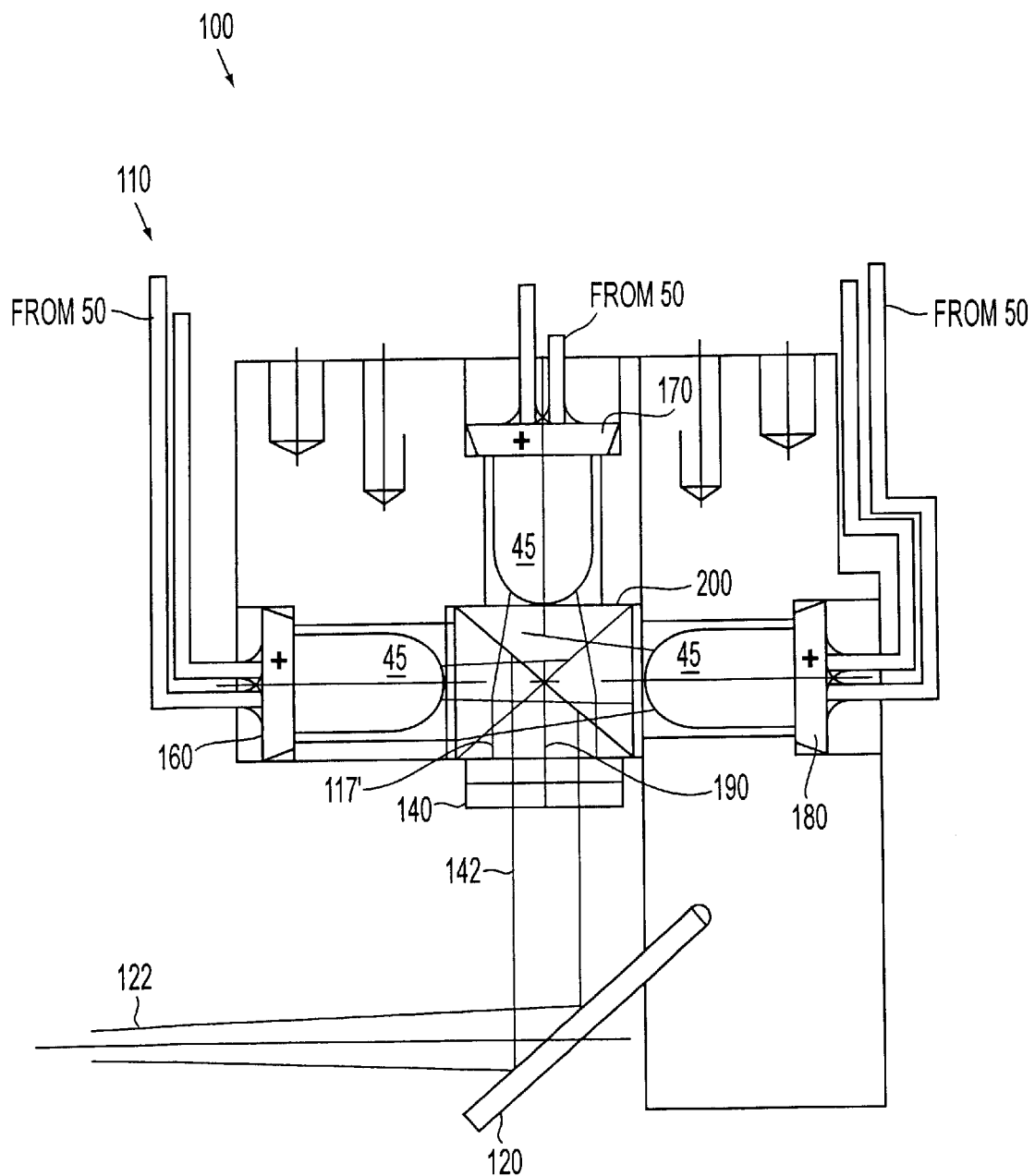
FIG. 9 is a side sectional view of a second exemplary embodiment of a portion of the illumination system of FIG. 1.

In a second exemplary embodiment of the light source 110, as shown in FIG. 9, a plurality of light emitting devices can be used to create a compound emitted beam of light 117' from the light source 110 which passes through the lens 140 to create a modified beam of light 142. By creating a compound emitted beam of light 117', the optical energy of the emitted beam of light 117' can thus be further increased in accordance with the number of light emitting devices 115 that are used. For illustrative purposes, a compound light source 110 having three light emitting devices 160, 170 and 180 will be described. However, it should be appreciated that the compound light source 110 can have a larger number of light emitting devices suitably arranged with the required beam combiners. Furthermore, it should also be appreciated that one or all of the light emitting devices 160, 170 and/or 180 can be the same as the light emitting device 115 of the first exemplary embodiment.

Also for illustrative purposes, the three light emitting devices 160, 170 and 180 will be described as emitting red, green and blue emitted beams of light 117, respectively, to create a white-color compound emitted beam of light 117'. However, it should be appreciated that the light emitting devices 160, 170 and 180 can emit any combination or density of colors to create a variably-colored beam of light 117'.

In various exemplary embodiments, the emitted beams of light 117 are aligned along a beam path 190 by a prism 200 located downstream of the light emitting devices 160, 170 and 180 but upstream of the lens 140. For illustrative purposes, any of the prisms described in the 889 patent can be used as the prism 200. Furthermore, it should be appreciated that any currently-available or later-developed device which can be used to combine the emitted beams of light 117 from light emitting devices 160, 170 and 180 to create a compound emitted beam of light 117' along the beam path 190 can be used in this invention.

In one exemplary device formed according to the systems and method described herein, the inventor has retrofitted a combination of commercially available red, green and blue emitting LEDs arranged in the exemplary configuration shown in FIG. 9, along with the exemplary illumination system configuration shown in FIG. 2, into one of the Quick Vision series of vision inspection machines available from Mitutoyo America Corporation (MAC), located in Aurora, Ill. This exemplary device achieved a fully operable range of illumination density when producing approximately white light in the field of view of the machine.

It should be appreciated that such a configuration is also controllable to produce various wavelength combinations other than white light. Furthermore, it should be appreciated that the dimension of the compound light source 110 in a direction normal to the plane of the figure need not be significantly greater than any of the light emitting devices 160, 170 and 180 or the prism 200, which, in various exemplary embodiments are, of similar dimensions. Thus, it should be appreciated that, in various embodiments of compound sources according to the systems and methods of this invention, output beam characteristics may be achieved which are not achievable using a beam provided by any single light emitting device. Furthermore, such compound sources may also be spaced closely together in various illumination systems, at a spacing comparable to that achievable with single light emitting devices.

Figure 10:
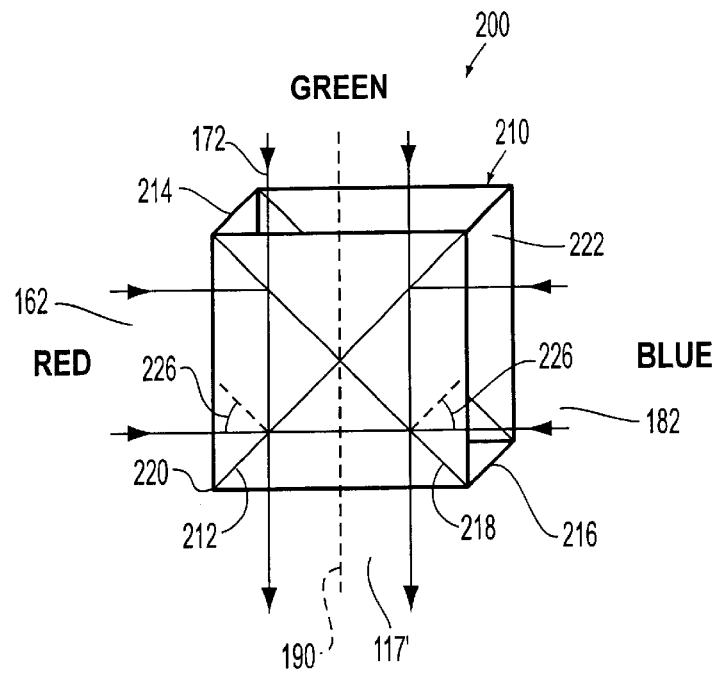
FIG. 10 is a diagram of a first exemplary embodiment of a cubic dichroic beamsplitter/combiner.
Figure 11:
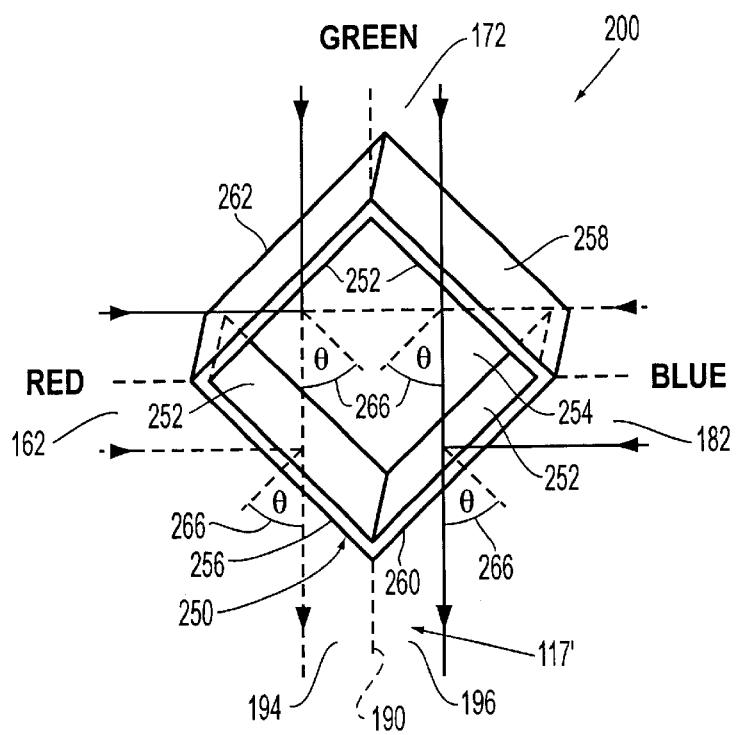
FIG. 11 is a diagram of a second exemplary embodiment of a dichroic beamsplitter/combiner of the invention.
Figure 12:
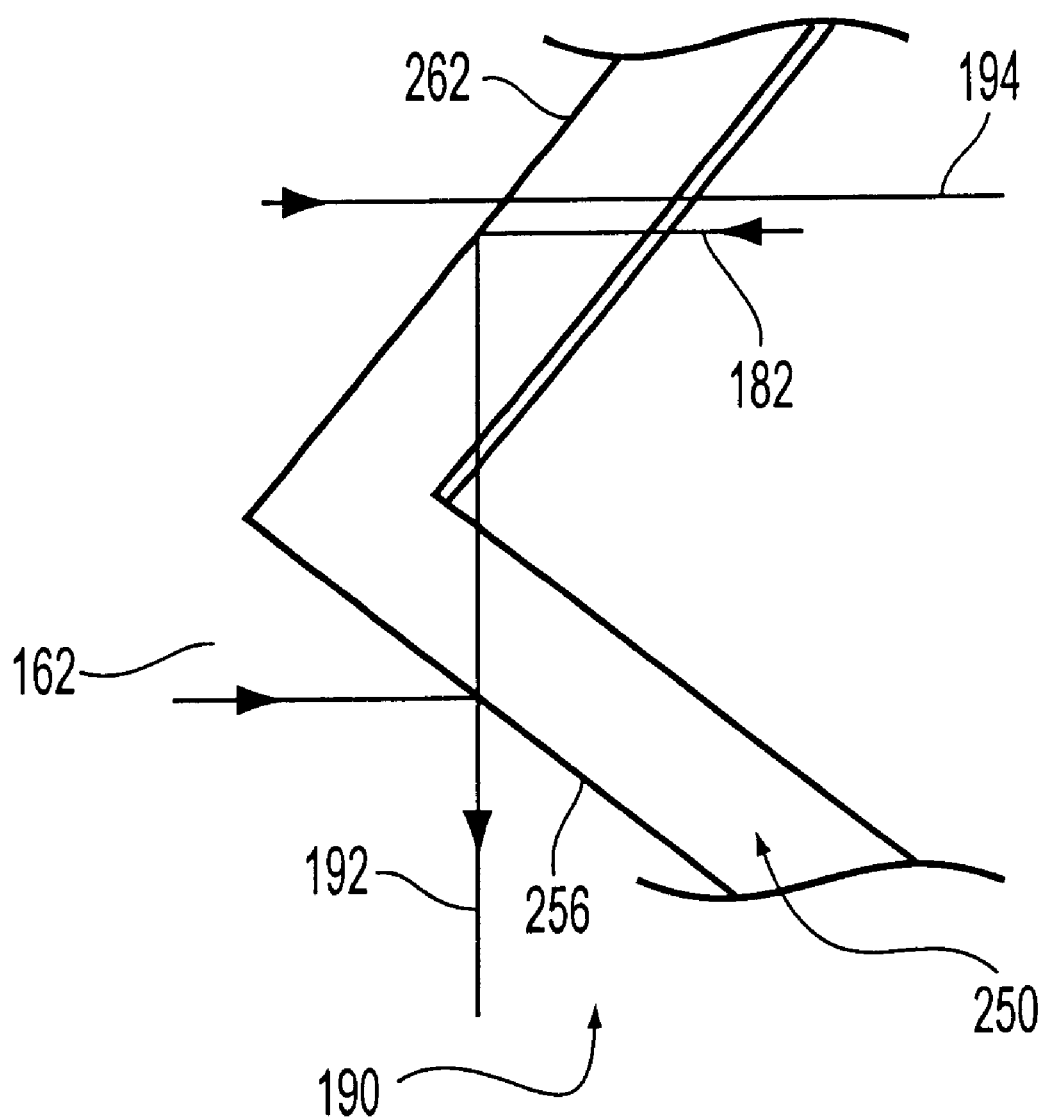
FIG. 12 is a diagram of a corner of the beamsplitter/combiner of FIG. 11.

FIGS. 10–12 show two exemplary embodiments of a prism disclosed in the incorporated 889 patent. As shown in FIG. 10, in one exemplary embodiment, the prism 200 is a cubic dichroic beamsplitter/combiner in a cube of glass 210. The beamsplitter/combiner 200 includes a dichroic blue-reflecting surface 212 with corners between a first opposite edge 220 and a second opposite edge 222 of the cube 210. A dichroic red-reflecting surface 218 is perpendicular to the blue-reflecting surface 212 and spans between a third edge 214 and a fourth edge 216. Both the red-reflecting surface 218 and the blue-reflecting surface 212 transmit green light.

A red beam of light 162 from the light emitting device 160 is introduced perpendicular to a first opposite edge 220 of the cube 210 and impinges on the blue-reflecting surface 212 and the red-reflecting surface 218 at a forty-five degree angle of incidence 226. The red beam of light 162 is redirected in a perpendicular direction along the beam path 190. A blue beam of light 182 from the light emitting device 180 is introduced and is perpendicular to a second opposite edge 222 and impinges on the blue reflecting surface 212 and the red reflecting surface 218 at a 45° angle of incidence 226. The blue beam of light is redirected in a perpendicular direction along the beam path 190. A green beam of light 172 from the light emitting device 170 is introduced and transmitted through both the blue reflecting surface 212 and the red-reflecting surface 218. The direction of the green beam of light 172 is also along the axis 190. As should be appreciated, the red, blue and green beam of light combine together to form a white color compound emitted beam of light 117'.

FIG. 11 is a second exemplary embodiment of the prism 200 as disclosed in the 889 patent. The prism 200 is a dichroic beamsplitter/combiner 200. The beamsplitter/combiner 200 includes a glass support structure 250 having four perpendicular walls 252 of equal dimensions joined edge to edge so that the walls 252 encompass a cubic volume 254. The glass support 250 may be constructed of optical grade glass, plastic or other suitable material.

The beamsplitter/combiner 200 has a first red-reflecting surface 256 and a second red-reflecting surface 258 opposite to and parallel to the first red-reflecting surface 256. A first blue-reflecting surface 260 is adjacent and perpendicular to the first red-reflecting surface 256. A second blue-reflecting surface 262 is opposite to and parallel to the first blue-reflecting surface 200. The surfaces 256, 258, 260, 262 are outward facing surfaces and are exposed to air on one side and to the glass support structure 250 on the other side.

The red-reflecting surfaces 256 and 258 have a conventional red-reflecting dichroic coating. Similarly, the blue-reflecting surfaces 260 and 262 have a conventional blue-reflecting dichroic coating. The coatings are optical thin-film coatings of dielectric materials applied in accordance with the teachings that are well-known to those skilled in the art.

For illustrative purposes, each half 194 and 196 of the beam of light 117' will be described. The red beam of light 162 is directed into a perpendicular first half 192 along the beam path 190 by the first red-reflecting surface 256. The red beam of light 162 is also directed into a perpendicular second half 196 along the beam path 190 by the second reflecting surface 258. The blue beam of light 182 is directed into a perpendicular second half 196 along beam path 190 by the first blue-reflecting surface 260. The blue beam of light 182 is directed into the perpendicular first half 194 along the beam path 190 by the second blue-reflecting surface 262.

The green beam of light 172 is introduced and transmitted through the dichroic surfaces 262, 258, 256, and 260 and through the support structure 250 resulting in the green beam of light 172 traveling in the same direction along the beam path 190. As a result, the red, green and blue beams of light 162, 172 and 182 combine to form the white-colored emitted beam of light 117'.

FIG. 12 is a diagram of a corner of a beamsplitter/combiner 200 of FIG. 11. The red beam of light 162 is reflected by the red-reflecting surface 256 into the perpendicular first half 192. The blue beam of light 182 is reflected by the blue-reflecting surface 262 into the perpendicular first half 192. The red beam of light 162, reflected by the second red-reflecting surface (see 258 of FIG. 11), transmits through the surface 262.

Beamsplitter/combiners, such as the "ColorBiner" prisms available from China Daheng Corporation, PO Box 9671, Beijing, 100086 PR CHINA, are also suitable commercially available components according to the systems and methods of this invention. Prisms may be fabricated with the particular physical dimensions required for a particular application.

The white-colored compound emitted beam of light 117' then passes through the lens 140 and the rest of the illumination system 100, similarly to the emitted beam of light 117. Thus, the description of the beams of light downstream from the prism 200 is not repeated here.

Figure 13:
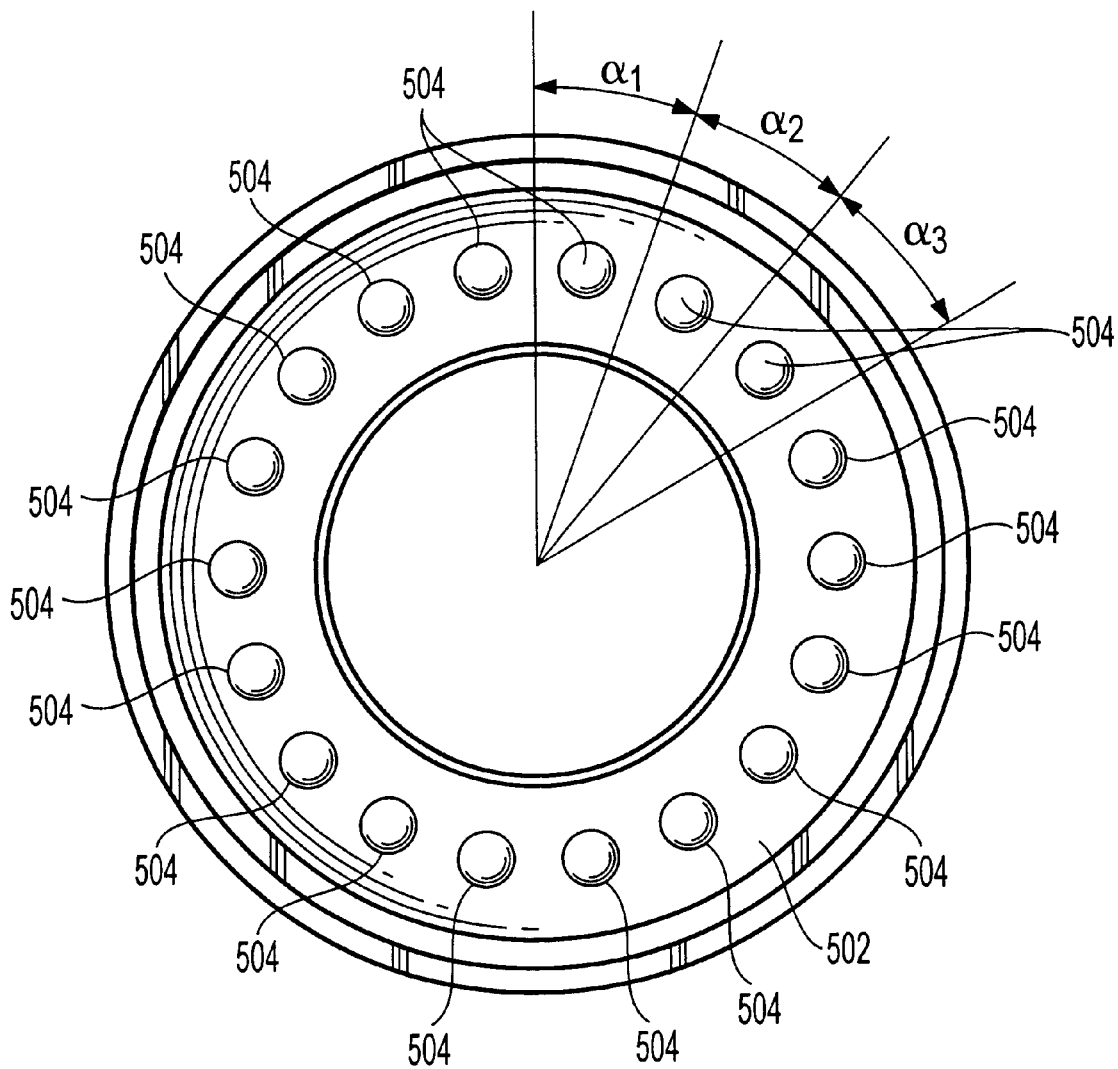
FIG. 13 is a plan view of a lighting system according to the related art.

As discussed above with reference to FIG. 8, the second reflective surface 130 projects the third modified beam of light 132 toward the stage 16. Further, as discussed with the compound multi-emitter light sources 110 of the second exemplary embodiment, a plurality of colors can be created while using a plurality of light emitting devices. Thus, as should be appreciated, the systems and methods according to this invention can project a variety of selectable and distinct colors of light along and any single azimuthal angle $\alpha_n$ and from a narrow azimuthal angle increment $\alpha$, which overcomes the deficiencies of the conventional system, as shown in FIG. 13, which must use a plurality of light sources 504 extended over a plurality of azimuthal angles $\alpha_{1-3}$ to create the same variety of color of light.

While this invention has been described in conjunction with the specific embodiments outlined above, it is evident that many alternatives, modifications and variations are apparent to those skilled in the art. For example the beam shaping principles described herein, the principles for orienting the non-emission areas of a light emitting device and/or light beam, and the principles for the construction and use of a compound source in a compact space to achieve a high light intensity using solid state lighting devices are all usable either separately or in combination to provide improved illumination density and illumination uniformity in an illumination field, while also providing a high degree of spatial addressability for both illumination intensity and color. The illumination principles of this invention are useable in conjunction with programmable lighting control systems, programmable automatic vision systems, and automatic or manual microscopic imaging and inspections systems and the like. Furthermore, the forgoing principles may be applied to any of the circular lighting system configurations included herein, or to analogous configurations which only partially surround an optical axis, but their utility is not limited to such configurations. Accordingly, the embodiments of the invention as set forth above are intended to be illustrated and not limiting. Various changes may be made without departing from the spirit and the scope of the invention.

What is claimed is:

1. An illumination apparatus, comprising:
   a first member carrying at least one compound light source and
   each compound light source comprising a plurality of controllable solid state light emitting devices and a beam combining element, each of the plurality of light emitting devices arranged to input respective input light beams into the beam combining element, wherein:
      each compound light source outputs a single output beam based on the input light beams and the characteristics of the beam combining element;
      the compound light source is usable to provide at least one characteristic of the output beam which is not achievable using a beam provided by any single one of the plurality of controllable solid state light emitting devices; and
      the output beam follows an optical path such that the apparatus is usable to illuminate the field of view of an imaging system.

2. The apparatus of claim 1, wherein the at least one characteristic of the single output beam comprises at least one of a maximum intensity and a wavelength combination.

3. The apparatus of claim 2, wherein the wavelength combination approximates white light.

4. The apparatus of claim 1, wherein the plurality of controllable solid state light emitting devices include a green light emitting device, a red light emitting device and a blue light emitting device.

5. The apparatus of claim 1, wherein each of the plurality of controllable solid state light emitting devices comprises one of a light emitting diode and a diode laser.

6. The apparatus of claim 1, wherein the beam combining element comprises at least one prism.

7. The apparatus of claim 6, wherein the at least one prism comprises a dichroic beamsplitter/combiner.

8. The apparatus of claim 1, wherein the first member is positionable to at least partially surround an optical axis of the imaging system, and the plurality of compound light sources are arranged on the first member such that the plurality of compound light sources is positionable to at least partially surround the optical axis of the imaging system.

9. The apparatus of claim 8, wherein at least some of the plurality of compound light sources are arranged at a common radius from an axis positionable to coincide with the optical axis of the imaging system, and at least some of the compound light sources arranged at the common radius are circumferentially spaced apart from each other at a center-to-center spacing which is less than 3 times the dimension of any individual solid state light emitting device in the circumferential direction.

10. The apparatus of claim 9, wherein at least some of the compound light sources arranged at a common radius are circumferentially spaced apart from each other at a center-to-center spacing which is less than 2 times the dimension of any individual solid state light emitting device in the circumferential direction.

11. The apparatus of claim 1, further comprising at least one illumination system optical path element which modifies at least one of a cross-section and a direction of the output beam to produce a modified output beam along the optical path.

12. The apparatus of claim 11, wherein the at least one illumination system optical path element comprises:
   a first reflective surface; and
   a second reflective surface, wherein the output beam is reflected by the first reflective surface onto the second reflective surface and the second reflective surface reflects a modified output beam of light along an angle of incidence usable to illuminate the field of view of a imaging system.

13. The apparatus of claim 12, wherein the first reflective surface and second reflective surface comprise portions of respective first and second annular surfaces, and the first and second annular surfaces are movable relative to each other along a common central axis which is normal to the plane of each annulus to control the angle of incidence.

14. The apparatus of claim 11, wherein the at least one illumination system optical path element comprises a lens which produces a modified output beam of approximately elliptical shape having a major axis and a minor axis.

15. The apparatus of claim 14, wherein the lens is one of a Fresnel lens and a cylindrical lens.

16. The apparatus of claim 14, wherein the lens is oriented such that in the region where the modified output beam illuminates the field of view of the imaging system the major axis is at least approximately aligned with a plane which is normal to an optical axis of the imaging system.

17. The apparatus of claim 16, wherein the at least one illumination system optical path element further comprises:
   a first reflective surface; and
   a second reflective surface comprising a portion of an annulus: wherein
      the modified output beam is received by the first reflective surface and reflected as a second modified output beam onto the second reflective surface, such that the major axis of the second modified output beam is at least approximately aligned with a plane parallel to the plane of the annulus and the second reflective surface reflects a third modified output beam along an angle of incidence usable to illuminate the field of view of a imaging system.

18. The apparatus of claim 17, wherein an emission area of the cross-section of the output beam is oriented such that the average intensity observable in the field of view when the apparatus illuminates the field of view of a imaging system using the at least one compound light source is greater than the middle of the range of average intensities observable corresponding to a full range of orientations of the emission area.

19. The apparatus of claim 1, wherein an emission area of the cross-section of the output beam is oriented such that the average intensity observable in the field of view when the apparatus illuminates the field of view of a imaging system using the at least one compound light source is greater than the middle of the range of average intensities observable corresponding to a full range of orientations of the emission area.

20. The apparatus of claim 1, wherein an emission area of the cross-section of the output beam is oriented such that the average intensity observable in the field of view when the apparatus illuminates the field of view of an imaging system using the at least one compound light source is at least 75% of the maximum average intensity observable for any orientation of the emission area.

21. The apparatus of claim 1, wherein when the at least one compound light source is used to illuminate the field of view of a imaging system, an approximately circular illumination field surrounds the field of view when illuminating a plane which is normal to an optical axis of the imaging system.

22. The apparatus of claim 1, wherein when the at least one compound light source is used to illuminate the field of view of a imaging system, an illumination field surrounding the field of view has a maximum dimension which is not more than twice the maximum dimension of the field of view when illuminating a plane which is normal to an optical axis of the imaging system.

23. The apparatus of claim 1, wherein the imaging system is a magnified imaging system.

24. An illumination apparatus comprising:
   a first member carrying at least one light source; and
   each light source comprising at least one controllable solid state light emitting device usable to provide an output beam following an optical path such that the apparatus is usable to illuminate the field of view of a imaging system;
   wherein an emission area of the cross-section of the output beam is oriented such that the average intensity observable in the field of view when the apparatus illuminates the field of view of the imaging system using the at least one light source is greater than the middle of the range of average intensities observable corresponding to a full range of orientations of the emission area.

25. The apparatus of claim 24, wherein an emission area of the cross-section of the output beam is oriented such that the average intensity observable in the field of view when the apparatus illuminates the field of view of the imaging system using the at least one light source is at least 75% of the maximum average intensity observable for any orientation of the emission area.

26. The apparatus of claim 24, further comprising at least one illumination system optical path element which modifies at least one of a cross-section and a direction of the output beam to produce a modified output beam along the optical path.

27. A method for illuminating a field of view of an imaging system having a first member carrying at least one compound light source, each compound light source comprising a plurality of controllable solid state light emitting devices and a beam combining element, each of the plurality of light emitting devices arranged to input respective input light beams into the beam combining element, the method comprising:
   outputting a single output beam from each compound light source based on the input light beams and the characteristics of the beam combining element;
   obtaining in the single output beam at least one characteristic that is not achievable using a beam provided by any single one of the plurality of controllable solid state light emitting devices; and
   directing the single output beam along an optical path to illuminate the field of view of the imaging system.

28. The method of claim 27, wherein the at least one characteristic of the single output beam comprises at least one of a maximum intensity and a wavelength combination.

29. The method of claim 28, wherein the wavelength combination approximates white light.

30. The method of claim 27, wherein the beam combining element comprises at least one prism with a dichroic beamsplitter/combiner.

31. The method of claim 27, wherein the first member is positionable to at least partially surround an optical axis of the imaging system, and the plurality of compound light sources are arranged on the first member such that the plurality of compound light sources is positionable to at least partially surround the optical axis of the imaging system.

32. The method of claim 27, further comprising modifying, with at least one illumination system optical path element, at least one of a cross-section and a direction of the output beam to produce a modified output beam along the optical path.

33. The method of claim 32, further comprising, with at least one illumination system optical path element comprising a first reflective surface and a second reflective surface:

reflecting the single output beam by the first reflective surface onto the second reflective surface; and reflecting the single output beam by the second reflective surface to create a modified output beam of light along an angle of incidence usable to illuminate the field of view of the imaging system, with at least one illumination system optical path element comprises a first reflective surface and a second reflective surface, wherein the output beam is reflected by the first reflective surface onto the second reflective surface and the second reflective surface reflects a modified output beam of light along an angle of incidence usable to illuminate the field of view of a imaging system.

34. The method of claim 27, wherein an emission area of the cross-section of the output beam is oriented such that the average intensity observable in the field of view when the apparatus illuminates the field of view of a imaging system using the at least one compound light source is greater than the middle of the range of average intensities observable corresponding to a full range of orientations of the emission area.

35. The method of claim 27, wherein when the at least one compound light source is used to illuminate the field of view of a imaging system, an illumination field surrounding the field of view has a maximum dimension which is not more than twice the maximum dimension of the field of view when illuminating a plane which is normal to an optical axis of the imaging system.

36. A method of illuminating a field of view of an imaging system having a first member carrying at least one light source, each light source comprising at least one controllable solid state light emitting device usable to provide an output beam following an optical path such that the apparatus is usable to illuminate the field of view of a imaging system, the method comprising:

outputting a beam of light wherein an emission area of the cross-section of the output beam is oriented such that the average intensity observable in the field of view when the apparatus illuminates the field of view of the imaging system using the at least one light source is greater than the middle of the range of average intensities observable corresponding to a full range of orientations of the emission area.

37. The method of claim 36, wherein an emission area of the cross-section of the output beam is oriented such that the average intensity observable in the field of view when the apparatus illuminates the field of view of the imaging system using the at least one light source is at least 75% of the maximum average intensity observable for any orientation of the emission area.

38. The method of claim 36, further comprising modifying, with at least one illumination system optical path element, at least one of a cross-section and a direction of the output beam to produce a modified output beam along the optical path.

* * * * *